United States Patent [19]

Bohlmann et al.

[11] Patent Number: 4,923,640
[45] Date of Patent: May 8, 1990

[54] PROCESS FOR THE PRODUCTION OF 17α-ETHINYL-17β-HYDROXY-18-METHYL-4,15-ESTRADIEN-3-ONE AND NEW INTERMEDIATE PRODUCTS FOR THIS PROCESS

[75] Inventors: Rolf Bohlmann; Henry Laurent; Helmut Hofmeister; Rudolf Wiechert, all of Berlin, Fed. Rep. of Germany

[73] Assignee: Schering Aktiengesellschaft, Berlin and Bergkamen, Fed. Rep. of Germany

[21] Appl. No.: 176,111

[22] Filed: Mar. 31, 1988

[30] Foreign Application Priority Data

Mar. 31, 1987 [DE] Fed. Rep. of Germany ....... 3710728

[51] Int. Cl.$^5$ .................. C07J 1/00; A61K 31/56
[52] U.S. Cl. .................. 552/625; 514/178; 514/182; 552/505; 552/644; 552/648
[58] Field of Search ............ 260/397.3, 397.4, 397.2; 514/177, 178, 182

[56] References Cited

U.S. PATENT DOCUMENTS

| 4,016,269 | 4/1977 | Hofmeister et al. | 260/397.3 |
| 4,036,695 | 7/1977 | Petzoldt et al. | 514/172 |
| 4,081,537 | 3/1978 | Hofmeister et al. | 514/182 |

OTHER PUBLICATIONS

Chemical Abstracts 75(1): 6182f 7/5/71.
Chemical Abstracts 8th Collective Index 1967-1971, "Gona-1,3,5(10),15-Tetraen-17-One-13-Ethyl—3 Methoxy".
Ichiro Minami et al., "New Synthetic Methods for α, β-Unsaturated Ketones, Aldehydes, Esters and Lactones by the Palladium-Catalyzed Reactions of Silyl Enol Ethers, Ketene Silyl Acetals, and Enol Acetates with Allyl Carbonates," Tetrahedron, vol. 42, No. 11, p. 2971, (1986).

Primary Examiner—Douglas W. Robinson
Assistant Examiner—Raymond J. Henley, III
Attorney, Agent, or Firm—Millen, White & Zelano

[57] ABSTRACT

A process for the production of 17α-ethinyl-17β-hydroxy-18-methyl-4,15-estradien-3-one is described comprising reacting a 17-enolester of formula II

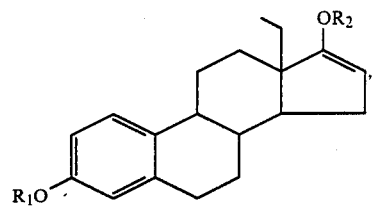

wherein
$R_1$ represents an alkyl radical with 1-3 carbon atoms and
$R_2$ represents an acyl or a trialkylsilyl group with 1-10 carbon atoms
under palladium catalysis, with compounds of formula II

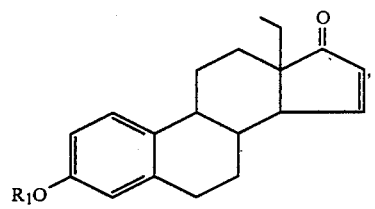

wherein
$R_1$ represents an alkyl radical with 1-3 carbon atoms, reducing the 17-keto group to the 17-hydroxy group in a manner known in the art, reducing the aromatic A-ring according to Birch, with liquid ammonia, to 3-methoxy-2,5(10),15-estratrien-17β-ol, reoxidizing the 17-hydroxy group to the 17-keto group, ethinylating the 17-keto group and splitting off the 3-enolether to form 17α-ethinyl-17β-hydroxy-18-methyl-4,15-estradiene-3-one.

14 Claims, No Drawings

PROCESS FOR THE PRODUCTION OF 17α-ETHINYL-17β-HYDROXY-18-METHYL-4,15-ESTRADIEN-3-ONE AND NEW INTERMEDIATE PRODUCTS FOR THIS PROCESS

BACKGROUND OF THE INVENTION

The invention relates to a new process for the production of 17α-ethinyl-17β-hydroxy-18-methyl-4,15-estradien-3-one (gestodene) and the new intermediate compounds for this process. Gestodene is an intensely active gestagen that can be used, for example, as a gestagen component in preparations for contraception (U.S. Pat. No. 4,081,537).

Several processes for the production of gestodene are already known. However, the introduction of the $\Delta^{15}$ double bond is a problem that has not yet been solved satisfactorily. Chemical dehydration methods result in low yields since the 18-methyl group inhibits the reaction (German laid-open specification No. 24 39 082). Enzymatic dehydration catalyzed by organisms is characterized by high synthesis' costs (German laid-open specification No. 24 56 068).

In Tetrahedron 42 (1986) 2971-2977, a process for dehydrating ketones by palladium-catalyzed reactions of enolacetates with allyl carbonates is described.

SUMMARY OF THE INVENTION

It is an object of this invention to provide an improved process for producing gestodene, e.g., in significantly higher yield and/or at lower cost than possible by the previously known syntheses.

Upon further study of the specification and appended claims, further objects and advantages of this invention will become apparent to those skilled in the art.

It has been discovered that surprisingly good results are achieved by the use of palladium-catalyzed dehydration for the introduction of the $\Delta^{15}$ double bond in gestodene. This process has the advantage that the dehydration is performed under relatively mild conditions and with higher yields than were obtained by use of the previously known processes.

These objects have been achieved by providing a process for the production of gestodene of Formula I

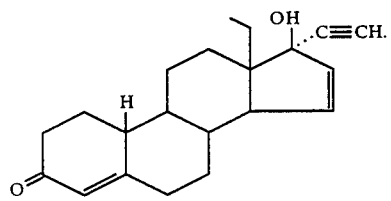

comprising reacting compounds of general Formula II

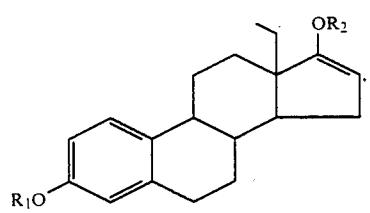

wherein
$R_1$ represents an alkyl radical with 1-3 carbon atoms and
$R_2$ represents an acyl or a trialkylsilyl group with up to 10 carbon atoms,
with palladium catalysis to form compounds of general Formula III

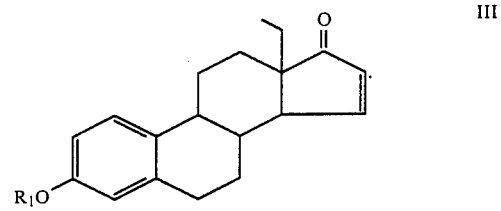

wherein
$R_1$ represents an alkyl radical with 1-3 carbon atoms, reducing the 17-keto group to form a 17-hydroxy group in a manner that is known in the art, reducing the aromatic A-ring by Birch reduction with liquid ammonia to form 3-methoxy-2,5(10),15-estratriene-17β-ol, reoxidizing the 17-hydroxy group to the 17-keto group, ethynylating the 17-keto group and splitting off the 3-enolether to form 17α-ethinyl-17β-hydroxy-18-methyl-4,15-estradiene-3-one.

In formulas II and III, $R_1$ represents an alkyl radical with 1 to 3 carbon atoms, the methyl and ethyl radicals being preferred. Radicals of organic, preferably hydrocarbon, carboxylic acids with 1-10 carbon atoms are suitable as acyl radicals $R_2$ in formula II; for example, alkanoyl, halogenated (e.g., F, Cl, Br, I) alkanoyl (both of which can be straight-chained or branched) and benzoyl, e.g., the acetyl, trifluoroacetyl, trimethylacetyl, propionyl, butyryl, heptanoyl and benzoyl radicals, the acetyl radical being preferred. The trimethylsilyl group, especially, is used as a trialkylsilyl group. The latter contains up to 24 C-atoms total in all three alkyl groups.

The palladium-catalyzed reaction of the corresponding enolacetates achieves good yields with trialkylsilyl- or trialkyltin (each of up to 24 C-atoms total) alkoxide (of 1-6 C-atoms) and allylcarbonate. Nitriles, especially benzo- and acetonitrile, are suitable solvents.

Suitable palladium catalysts include palladium metal, palladium compounds and salts, e.g., palladium acetate, and palladium complexes, e.g., tetrakis(triphenylphosphine) palladium(O) or bis/di-1,2-diphenylphosphine ethane/palladium(O). Generically, suitable reaction times are 0.5-10 hours.

Starting materials of Formula II can all be made from known materials using conventional reactions, e.g., analogous to Example 1 and the reference cited therein.

In a preferred embodiment, the enol derivative of Formula II is refluxed in acetonitrile with catalytic quantities of palladium acetate (e.g., 2-20 g/mol enol derivative) and catalytic quantities of tributyltin methoxide (e.g., 4-60 g/mol) in the presence of allylmethylcarbonate in excess (e.g., 20-200 g/mol). After a reaction period of 1-3 hours (60°-140° C.), the dehydrated product can be separated and purified chromatographically.

The further processing of the compounds of general formula III into gestodene of formula I is explained in more detail with the help of the following diagram:

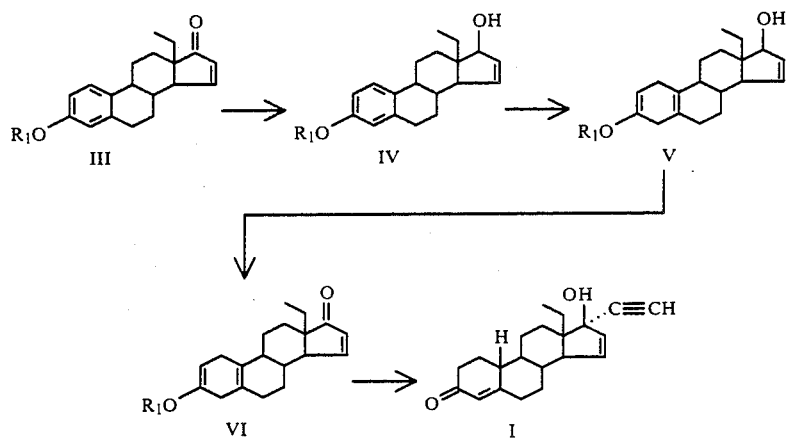

The 17-ketone can be reduced, for example, with sodium borohydride in the presence of cerium(III) ions J. L. Luche, (J. Am. Chem. Soc. 100 (1978) 2226); after, e.g., Birch reduction of the aromatic A-ring (Wilds, A. L. and Nelson, N. A. J. Am. Chem. Soc. 75(1953) 5366) and reoxidation of the 17β-alcohol, for example with manganese dioxide (Sondheimer et al. J. Am. Chem. Soc. 77(1955) 4145), the 17-ketone is ethinylated (J. H. Saunders, Org. Syn. Coll. Vol. 3 (1955) 416) and then the acid enolether is split off (Wilds, A. L. and Nelson, N. A. J. Am. Chem. Soc. 75(1953) 5366), and the resultant gestodene of Formula I is obtained.

All compounds of this invention and the full scope and individual reactions of the process of this invention thus are very useful for preparing gestodene in the sequence of reaction steps disclosed herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

17-Acetoxy-3-methoxy-18-methyl-1,3,5(10),16-estratetraene 30 g of 3-methoxy-18-methyl-1,3,5(10)-estratrien-17-one [J. Org. Chem. 40 (1975) 681] is stirred for 22 hours at 120° C. in 200 ml of isopropenylacetate with 1.5 g of p-toluenesulfonic acid. It is then diluted with ethyl acetate, washed with sodium carbonate and a common salt (NaCl) solution, dried over sodium sulfate and concentrated. After chromatography, 27.6 g of 17-acetoxy-3-methoxy-18-methyl-1,3,5(10),16-estratetraene with a melting point of 105°–106° C. is obtained.

EXAMPLE 2

3-Methoxy-18-methyl-1,3,5(10),15-estratetraen-17-one 3.4 g of 17-acetoxy-3-methoxy-18-methyl-1,3,5(10),16-estratetraene is refluxed for 1.5 hours in 50 ml of acetonitrile with 2.3 ml of allylmethylcarbonate, 220 mg of palladium acetate and 580 microliters of tributyltin methoxide. The reaction mix is then diluted with water, extracted with dichloromethane and concentrated under vacuum. After chromatographic purification, 2.1 g of 3-methoxy-18-methyl-1,3,5(10),15-estratetraen-17-one with a melting point of 158°–160° C. is obtained.

EXAMPLE 3

3-Methoxy-18-methyl-1,3,5(10),15-estratetraen-17β-ol 4.7 g of 3-methoxy-18-methyl-1,3,5(10),15-estratetraen-17-one in 30 ml of tetrahydrofuran and 45 ml of methanol are mixed with 6.8 g of cerium(III)-chloride heptahydrate. At 0° C., 1.0 g of sodium borohydride is added, in portions. After 1 hour, the reaction mixture is put in ice/water. The precipitated product is suctioned off, dissolved in ethyl acetate, washed with water and dried. 4.5 g of 3-methoxy-18-methyl-1,3,5(10),15-estratetraen-17β-ol is obtained as a foam.

EXAMPLE 4

3-Methoxy-18-methyl-2,5(10),15-estratrien-17β-ol 5.0 g of 3-methoxy-18-methyl-1,3,5,(10), 15-estratetraen-17β-ol in 250 ml of tetrahydrofuran is added to 250 ml of liquid ammonia at −78° C. It is mixed with 30 ml of ethanol and 1.5 g of lithium is added in small portions. After the reaction is completed, the ammonia is allowed to evaporate, water is carefully instilled during cooling, the product is diluted with ethyl acetate, and the organic phase is washed with water and dried. 4.7 g of 3-methoxy-18-methyl-2,5(10),15-estratrien-17β-ol is obtained as a foam.

EXAMPLE 5

3-Methoxy-18-methyl-2,5(10),15-estratrien-17-one 4.7 g of 3-methoxy-18-methyl-2,5(10),15-estratrien-17β-ol is refluxed for 18 hours in 250 ml of chloroform and 35 ml of t-butanol with 10 g of manganese dioxide. The product is suctioned off over Celite, rewashed with chloroform and concentrated under reduced pressure. After chromatographic purification on silica gel with hexane/ethyl acetate, 4.1 g of pure 3-methoxy-18-methyl-2,5(10),15-estratrien-17-one with a melting point of 89°–91° C. is obtained.

EXAMPLE 6

17α-ethinyl-17β-hydroxy-18-methyl-4,15-estradien-3-one (Gestodene)

Acetylene is introduced into a solution of 40 ml of n-butyllithium (15% in hexane) in 100 ml of tetrahydrofuran at 0° C. for 30 minutes, and then 4.0 g of 3-methoxy-2,5(10),15-estratrien-17-one in 40 ml of tetrahydrofuran is instilled. After 45 minutes, 16 ml of semi-concentrated hydrochloric acid is added to the reaction mixture and it is stirred for 45 minutes at room temperature. The product is then diluted with ethyl acetate, washed with water and dried. After recrystallization from ethyl acetate, 2.4 g of 17α-ethinyl-17β-hydroxy-18-methyl-4,15-estradien-3-one with a melting point of 196° C. is obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of a compound of the formula III

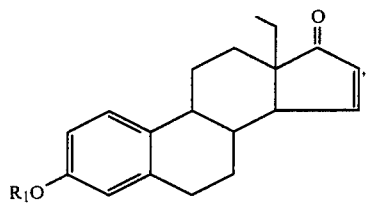

wherein R₁ is alkyl of 1–3 carbon atoms, comprising reacting a 17-enolester of formula II

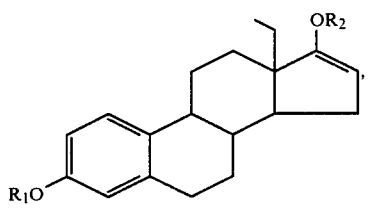

wherein
R₁ is alkyl of 1–3 carbon atoms and
R₂ represents an acyl or a trialkylsilyl group with up to 10 carbon atoms,
with a palladium catalyst to form a compound having the formula III.

2. A process for the production of 17-ethinyl-17β-hydroxy-18-methyl-4,15-estradien-3-one of the formula I

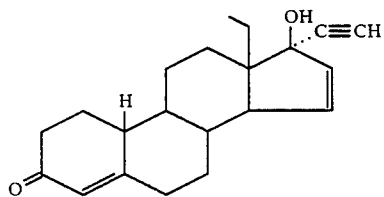

comprising reaction a 17-enolester of the formula II,

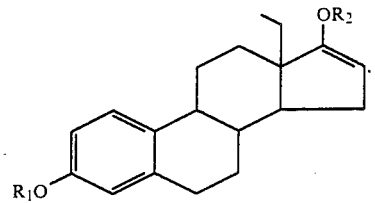

wherein
R₁ is C₁₋₃-alkyl and
R₂ represents an acyl or a trialkylsilyl group with up to 10 carbon atoms,
with a palladium catalyst to form a compound having the formula III

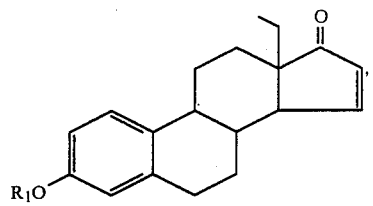

wherein R₁ represents an alkyl radical with 1–3 carbon atoms, reducing the 17-keto group in the compound of formula III to form a corresonding compound with a 17-hydroxy group, reducing the aromatic A-ring of the resultant 17-OH compound by a Birch reduction with liquid ammonia to form 3-methoxy-2,5(10),15-estratriene-17β-ol, reoxidizing the 17-hydroxy group of the 17β-ol compound to form the corresponding compound having a 17-keto group, ethinylating said 17-keto group and splitting off a 3-enolether to form 17-ethinyl-17β-hydroxy-18-methyl-4,15-estradiene-3-one.

3. A process of claim 1 wherein the palladium catalyst is palladium acetate.

4. A process of claim 1 wherein R₁ is methyl or ethyl and R₂ is acetyl.

5. A process of claim 1 conducted in the presence of a trialkylsilyl- or trialkyltin alkoxide and allylcarbonate.

6. A process of claim 2 wherein the palladium catalyst is palladium acetate.

7. A process of claim 2 wherein R₁ is methyl or ethyl and R₂ is acetyl.

8. A process of claim 2 conducted in the presence of a trialkylsilyl- or trialkyltin alkoxide and allylcarbonate.

9. A compound of the formula

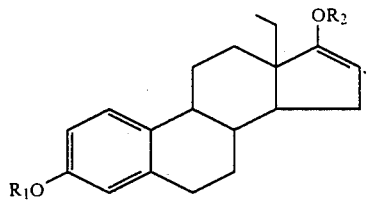

wherein
R₁ is C₁₋₃-alkyl and
R₂ is C₁₋₁₀-alkanoyl, C₁₋₁₀-haloalkanoyl, benzoyl, or trialkylsilyl of up to 10 C-atoms.

10. 17-Acetoxy-3-methoxy-18-methyl-1,3,5(10)-16-estratetraene, a compound of claim 9.

11. A compound of the formula

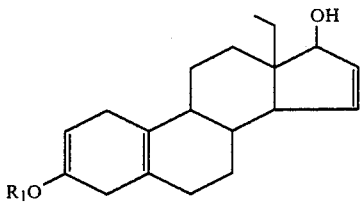 V
wherein
R₁ is $C_{1-3}$-alkyl.
12. 3-Methoxy-18-methyl-2,5(10),15-estratrien-17β-ol, a compound of claim 11.
13. A compound of the formula
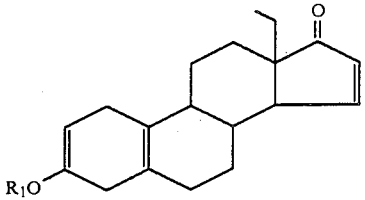 VI
wherein
R₁ is $C_{1-3}$-alkyl.
14. 3-Methoxy-18-methyl-2,5(10),15-estratrien-17-one, a compound of claim 13.
* * * * *